United States Patent [19]

Bhargava et al.

[11] Patent Number: 4,942,042

[45] Date of Patent: Jul. 17, 1990

[54] ANTI-DIARRHEA COMPOSITIONS

[75] Inventors: Hridaya Bhargava, Sharon, Mass.; Jacques Jutteau, Saint-Cloud, France

[73] Assignee: Societe de Conseils de Recherches et d'Applications Scientifiques (S. C. A. S.), France

[21] Appl. No.: 239,034

[22] Filed: Aug. 29, 1988

Related U.S. Application Data

[63] Continuation of Ser. No. 860,628, May 7, 1986, abandoned.

[30] Foreign Application Priority Data

May 15, 1985 [GB] United Kingdom ................ 8512345

[51] Int. Cl.$^5$ ................ A61K 31/12; A61K 33/06; A61K 33/14
[52] U.S. Cl. .................................. 424/683; 424/684; 424/679; 424/680; 424/717
[58] Field of Search ............... 424/683, 684, 679, 680, 424/717

[56] References Cited

U.S. PATENT DOCUMENTS 3,928,574 12/1975 Phillips ................. 514/867

OTHER PUBLICATIONS

*Handbook of Nonprescription Drugs*, Fifth Edition, published by Amer, Pharm, Assoc., Wash. D.C., pp. 31 & 32.

*Primary Examiner*—Frederick E. Waddell
*Attorney, Agent, or Firm*—Lucas & Just

[57] ABSTRACT

An anti-diarrhea composition comprises diarrhea symptom-reducing amounts of a powdered absorptive material capable of absorbing pathogenic intestinal bacteria, a sodium salt, a potassium salt and a sugar. The absorptive material may be Smectite or mormoiron attapulgite. The salts are preferably NaCl and KCl, with NaHCO$_3$ also being present. Suitable sugars are glucose and dextrose. The composition may also contain a suspending agent, a coloring agent, a flavoring agent and a sweetening agent. It may be packaged in solid form for admixture with water prior to administration and is preferably moisture protected, for example by the nature of the packaging or by inclusion of a dessicant. The absorptive material may be packaged separately from the salts and sugar. On admixture with water for administration, the composition preferably contains, per liter, 2.5 to 15 g of absorptive material, 10 to 30 g of glucose, 60 to 120 mEq of Na$^+$, 10 to 50 mEq of HCO$^-$ and 10 to 30 mEq of K$^+$.

12 Claims, No Drawings

ANTI-DIARRHEA COMPOSITIONS

This is a continuation of application Ser. No. 860,628, filed May 7, 1986, now abandoned.

The invention relates to anti-diarrhea compositions.

Diarrhea is commonly treated either by administering an absorptive material, which absorbs pathogenic bacteria, digestive enzymes, toxins, and nutrients from the gastrointestinal tract; or by administering an oral electrolyte/sugar replacement fluid such as that recommended by the World Health Organization containing, per liter, 20 g glucose, 90 mEq sodium, 30 mEq bicarbonate and 20 mEq potassium (Chatterjee et al. (1978) Arch. Dis. Child. 53, 284).

The invention provides an anti-diarrhea composition containing diarrhea symptom-reducing amounts of a thermally activated, finely powdered, hydrous magnesium aluminium silicate clay as absorptive material capable of absorbing pathogenic intestinal bacteria, a sodium salt, a potassium salt and a sugar.

The absorptive material is preferably also capable of absorbing diarrhea-associated viruses, intestinal toxins and gases. A number of suitable absorptive materials are known. One such clay is known in its unactivated form as Smectite, and has the formula $Si_8Al_4O_{20}OH_4$. Other such clays are argillaceous clays, for example the clay known in its unactivated form as mormoiron attapulgite further named ATTA under its activated form. This is also well-known as an anti-diarrhea absorptive material.

The absorptive material is provided in an amount recognized as effective in the treatment of diarrhea, in a package whose contents are to be reconstituted with 200 ml of water. The absorptive material is provided in an amount such that, following reconstitution, it is present in a concentration of 2.5–15 g/l.

The electrolyte/sugar composition contains a potassium salt, a sodium salt, and a sugar.

Preferably, the two salts are sodium chloride and potassium chloride, and the sugar is glucose or dextrose. The composition preferably also contains a bicarbonate salt such as sodium bicarbonate.

Since the electrolyte/sugar is normally transported in a dehydrated, powdered state, it is preferred that some measure be taken to prevent moisture from causing solidification of the powder, which would interfere with fluid reconstitution. This can be achieved by enclosing the powdered material in a moisture-resistant package such as one of aluminium alloy, or by including a dessicating agent, or by treating the electrolyte/sugar in a way which inhibits moisture absorption, for example the crystal formation method described in U.S. Pat. specification No. 2642335. The latter two approaches offer the advantage of permitting the use of low-cost packaging, e.g., waxed paper, which is not completely moisture-resistant. The electrolyte/sugar can be provided in the same package as the absorptive material or in a separate package. (In the case of separate packages moisture resistance is desirable for the absorptive material as well).

Generally, the electrolytes and sugar are provided in amounts recognized as effective in the treatment of diarrhea. Each package is formulated to be reconstituted with 200 ml of water. The electrolyte and sugar components are preferably provided in amounts such that, following reconstitution, they are present in the following concentration ranges: glucose: 10–30 g/l; sodium: 60–120 mEq/l; bicarbonate: 10–50 mEq/l; potassium: 10–30 mEq/l.

In preferred embodiments, the composition also contains a suspending agent capable of facilitating the suspension or homogeneous dispersion of the absorptive material in water; in the absence of such an agent, clays such as Smectite tend to settle at the bottom of a container when combined with water, rendering homogeneous administration difficult. The suspending agent may be, for example, a hydrocolloid (such as sodium carboxy methyl cellulose, xanthan gum, hydroxy propyl methyl cellulose, polyethylene glycol, a dextrin, gum karaya, gum tragacanth, gum acacia, gum guar or a polysaccharide), a polyol (such as glycerin, propylene glycol or sorbitol) or a surfactant (such as dioctyl sulfosuccinate, polysorbate-40 or sorbitan monooleate).

The suspending agent is provided in the same package as the absorptive material, in an amount which, when the composition is reconstituted, is present at a concentration of 0.25–1.0 g/l, in the case of naturally occurring hydrocolloids such as xanthan gum, and 1.0–5.0 g/l, in the case of the other classes of agents. In some instances, more than one suspending agent can be used in conjunction.

In addition to the components listed above, the compositions of the invention can also contain colouring, flavouring and sweetening agents.

In order to prepare a dry composition for packaging and reconstituting, the suspending agent or agents are first placed in mixing means, e.g., a P-K blender or cube blender. The absorptive material is then added, and mixing carried out for 10–20 minutes. The salts and sugar are then added, one at a time, and mixing carried out for an additional 10–20 minutes. Any desired additional ingredients are then added and mixed, and the dry composition enclosed, in amounts to be reconstituted to 200 ml, in sealed waxed paper, plastic, or foil packages.

As mentioned above, an additional previous step can be the crystallization water-resistance treatment of the salts, as described in U.S. Pat. specification No. 2642335.

In use individual packages are opened, mixed with measured amounts of water, and taken orally. The number of packages administered per day will depend on such factors as the age and body weight of the patient, and the severity of the diarrhea.

Generally, if a child weighs less than 5 kg, dosage is one package/day, with ½ package given initially, followed by ⅓ package every 8 hours. For children weighing between 5 and 10 kg, dosage is 1–2 packages per day, and for children weighing more than 10 kg, dosage is 2 packages per day, with one package being given initially, followed by ½ package every 6 hours.

Below are examples of compositions of the invention. Each is to be reconstituted in 200 ml of water. Composition 2 actually gives four slightly different formulas, A-D, while each of compositions 3 and 4 gives 10 different formulae, A-J. All units are in term of grams per package.

| COMPOSITION 1 | |
| --- | --- |
| Ingredient | Grams per Packet |
| Smectite | 1.0 |
| Sodium Chloride* | 0.7 |
| Potassium Chloride* | 0.3 |
| Sodium Bicarbonate* | 0.5 |

-continued

COMPOSITION 1

| Ingredient | Grams per Packet |
|---|---|
| Glucose Monohydrate* | 4.0 |

*Equivalent to 18 mEq Sodium/200 ml, 4 mEq Potassium per 200 ml, 6 mEq Bicarbonate 200 ml and 4.0 gm Glucose/200 ml.

COMPOSITION 2

| Ingredient | A | B | C | D |
|---|---|---|---|---|
| Smectite | 1.0 | 1.0 | 1.0 | 1.0 |
| Sodium Chloride | 0.7 | 0.7 | 0.7 | 0.7 |
| Potassium Chloride | 0.3 | 0.3 | 0.3 | 0.3 |
| Sodium Bicarbonate | 0.5 | 0.5 | 0.5 | 0.5 |
| Glucose Monohydrate | 4.0 | 4.0 | 4.0 | 4.0 |
| Xanthan Gum | — | — | — | 0.05–0.2 |
| Hydroxy Propyl Methyl Cellulose 4000 cps (Methocel) | — | — | 0.5–1.0 | — |
| Carbomer 934 | — | 0.2–0.5 | — | — |
| Sodium Carboxy Methyl Cellulose | 0.2–1.0 | — | — | — |

COMPOSITION 3

| Ingredient | A | B | C | D | E | F | G | H | I | J |
|---|---|---|---|---|---|---|---|---|---|---|
| Smectite | 1.0 | 1.0 | 1.0 | 1.0 | 1.0 | 1.0 | 1.0 | 1.0 | 1.0 | 1.0 |
| Sodium Chloride | 0.7 | 0.7 | 0.7 | 0.7 | 0.7 | 0.7 | 0.7 | 0.7 | 0.7 | 0.7 |
| Potassium Chloride | 0.3 | 0.3 | 0.3 | 0.3 | 0.3 | 0.3 | 0.3 | 0.3 | 0.3 | 0.3 |
| Sodium Bicarbonate | 0.5 | 0.5 | 0.5 | 0.5 | 0.5 | 0.5 | 0.5 | 0.5 | 0.5 | 0.5 |
| Glucose Monohydrate | 4.0 | 4.0 | 4.0 | 4.0 | 4.0 | 4.0 | 4.0 | 4.0 | 4.0 | 4.0 |
| Gum Karaya | 0.05 | — | — | — | — | — | — | 0.1 | — | 0.1 |
| | 0.2 | | | | | | | | | |
| Gum Guar | — | 0.05– 2.0 | — | — | — | — | — | — | 1.0 | — |
| Acacia | — | — | 0.5– 2.0 | — | 0.5– 2.0 | — | 0.79 | — | — | 0.5 |
| Polyethylene Glycol 6000 | — | — | — | 2.0 | — | — | 3.0 | — | — | — |
| Glycerin USP | 0.5 | 0.5 | 0.5 | — | — | — | — | — | 0.5 | — |
| Sodium Dioctysulphosuccinate | 0.1 | 0.1 | 0.1 | — | — | — | — | — | 0.01 | — |
| Polysorbate-40 | — | — | — | — | 0.1 | — | — | 0.05 | — | — |
| Maltodextrin | — | — | — | — | — | 1.0 | 0.1 | — | — | 0.5 |

COMPOSITION 4

| Ingredient | A | B | C | D | E | F | G | H | I | J |
|---|---|---|---|---|---|---|---|---|---|---|
| Smectite | 1.0 | 1.0 | 1.0 | 1.0 | 1.0 | 1.0 | 1.0 | 1.0 | 1.0 | 1.0 |
| Sodium Chloride | 0.7 | 0.7 | 0.7 | 0.7 | 0.7 | 0.7 | 0.7 | 0.7 | 0.7 | 0.7 |
| Potassium Chloride | 0.3 | 0.3 | 0.3 | 0.3 | 0.3 | 0.3 | 0.3 | 0.3 | 0.3 | 0.3 |
| Sodium Bicarbonate | 0.5 | 0.5 | 0.5 | 0.5 | 0.5 | 0.5 | 0.5 | 0.5 | 0.5 | 0.5 |
| Glucose Monohydrate | 4.0 | 4.0 | 4.0 | 4.0 | 4.0 | 4.0 | 4.0 | 4.0 | 4.0 | 4.0 |
| Xanthan Gum | 0.1 | 0.1 | — | — | 0.1 | 0.1 | 0.1 | — | — | — |
| Sodium GMC | 0.1 | — | 0.1 | 0.2 | — | 0.1 | — | — | — | — |
| Glycerin | — | 0.1 | 0.1 | — | — | — | — | 0.5 | — | 0.5 |
| Polyethylene glycol 6000 | — | — | — | 2.0 | — | — | — | 1.0 | 5.0 | — |
| Maltodextrin | — | — | — | — | 0.5 | 0.5 | 0.5 | — | 2.0 | 2.0 |
| Cabosil M-5 | — | — | — | — | 0.1 | — | 0.1 | — | — | — |
| Calcium Chloride | — | — | — | — | — | 0.2 | — | — | 0.2 | 0.2 |
| Sodium Benzoate | 0.1 | — | — | 0.1 | 0.1 | 0.1 | 0.1 | — | 0.1 | 0.1 |
| Methocel 4000 | — | — | — | — | — | — | — | — | — | 0.75 |

-continued

COMPOSITION 4

| Ingredient | A | B | C | D | E | F | G | H | I | J |
|---|---|---|---|---|---|---|---|---|---|---|
| Gum Tragacanth | — | — | — | — | — | — | — | 0.5 | — | — |

COMPOSITION 5

| Ingredient | Vendor | Amount Weight/Packet | % Weight/Packet |
|---|---|---|---|
| Sodium Citrate Dihydrate | Pfizer | 0.60 g | 8.16 |
| Potassium Chloride | Morton Salt Company | 0.30 g | 4.08 |
| Sodium Chloride | Morton Salt Company | 0.66 g | 8.98 |
| Dextrose Monohydrate | Corn Products (CPI) | 4.00 g | 54.42 |
| Xanthan Gum | Kelco Inc | 0.10 g | 1.36 |
| Maltodextrin | Grain Processing Corporation | 0.50 g | 6.81 |
| Calcium Triphosphate | Stauffer Chem. | 0.09 g | 1.22 |
| Sodium Benzoate | Mallinckrodt Inc | 0.10 g | 1.36 |
| Activated Smectite | Ipsen-Beaufour | 1.00 g | 13.61 |
| | | 7.35 g | 100.00 |

In another aspect, the invention provides a method of treating diarrhea in a human patient, involving administering to the patient diarrhea symptom reducing amounts of first and second compositions, the first and second compositions being admixed together, or administered separately within thirty minutes of each other, the first composition containing a powdered absorptive material capable of absorbing pathogenic intestinal bacteria, and the second composition containing a sodium salt, a potassium salt, and a sugar, at least the second composition being administered to the patient admixed with water.

The invention provides relief from the symptoms of diarrhea, while at the same time replenishing electrolytes, sugar, and fluid. Despite the simultaneous or near-simultaneous administration of the electrolyte/sugar and the absorptive material, the electrolytes and sugar are not absorbed to a deleterious degree by the absorptive material. Administration of both absorptive material and electrolyte/sugar is more effective in controlling diarrhea than the administration of electrolyte/sugar alone.

The electrolyte/sugar and absorptive compositions do not need to be admixed together prior to administration; alternatively, the two can be administered separately, in immediate succession or within thirty minutes of each other. This method, like the method involving providing both compositions admixed together, is effective to both replace fluids and electrolytes, and absorb harmful gases, viruses, bacteria, and toxins, while avoiding deleterious absorption, by the absorptive material, of the beneficial electrolytes and sugar.

Sequential administration of a reconstituted electrolyte composition and powdered attapulgite was carried out on infant children, and shown to provide superior diarrhea symptom treatment, compared to electrolyte treatment alone, in the study described below.

100 children aged between 1 and 24 months and hospitalized for acute diarrhea requiring oral rehydration solution ("ORS") were divided into two groups of 50 patients each, balanced in terms of age and severity of symptomatology.

Children in group I received ORS only. Rehydration salts were presented in the form of envelopes for dissolution in one liter drinking water before use. The composition is shown in the following table:

| CONSTITUENTS | QUANTITY in g/l |
| --- | --- |
| Nacl | 3.5 |
| CO₃HNa | 2.5 |
| KCl | 1.5 |
| Glucose | 20.0 |
| MOLARITY | |
| CONSTITUENTS | mmol/l IN WATER |
| Na | 90 |
| K | 20 |
| Cl | 80 |
| CO₃H | 30 |
| Glucose | 111 |

Children in group II received this same solution, along with 1-2 envelopes/day containing 3 g attapulgite. Dosage varied with body weight as described earlier.

Six treatment evaluation criteria were chosen:
1. The number of stools after 48 hours treatment,
2. The number of stools per 24 hours after 2 days treatment,
3. Daily weight gain,
4. Duration of treatment,
5. Frequency of relapse,
6. Side-effects, in particular, constipation.

Finally, cost of daily treatment was estimated.

Analysis of the population studied

Distribution by sex:
  female: 51
  male: 49
Distribution by age:
  2-12 months: 51
  13-24 months: 49
Concurrent symptomatology:
  fever: 26
  vomiting: 48

The number of stools per day for each group prior to treatment is given in the following table.

| | No. of stools | |
| --- | --- | --- |
| Group | 3-6 | 7-10 |
| ORS | 34 (68%) | 16 (32%) |
| ORS + ATTA | 44 (88%) | 6 (12%) |

Dosages

Dosages were as follows:
ORS:
  ¼ to ½ liter for children younger than 6 months;
  ½ to 1 liter for children between 6 and 24 months.
Attapulgite:
  1 envelope/day for children weighing less than 5 kg.
  2 envelopes/day for children weighing more than 5 kg.

Results are given as a function of the evaluation criteria defined above.

Results (1) Characteristics of Stools after 48 hours treatment

Classification was as follows: absolutely liquid; semi-liquid; soft; normal.

Results are shown in the following table:

| | ORS (n = 50) | | ORS + ATTA (n = 50) | |
| --- | --- | --- | --- | --- |
| | No. | % | No. | % |
| Liquid stools | 26 | 52 | 10 | 20 |
| Semi-liquid stools | 10 | 20 | 14 | 28 |
| Soft stools | 11 | 22 | 18 | 36 |
| Normal stools | 3 | 6 | 8 | 16 |

(2) Number of stools per day after 48 hours treatment

The mean daily frequency of stools in both groups, upon admission and after 48 hours treatment, is given in the following table:

| | MEAN NUMBER OF STOOLS/DAY | |
| --- | --- | --- |
| Product | Upon admission | After 48 hours treatment |
| ORS | 6 | 4 |
| ORS + ATTA | 6 | 3 |

After 48 hours treatment, 26 infants (52%) in the ORS group still had very liquid stools. Such diarrhea no longer threatened the vital prognosis.

In the ORS+ATTA group, only 10 infants (20%) still presented liquid stools. We also note complete normalization of stools in 3 cases in the ORS group (6%) versus 8 cases (16%) with the combination treatment. At the same time, there was a greater reduction in the frequency of stools in the group receiving the combination (3 stools/day, rather than 6) than in the ORS group (4 stools/day, rather than 6).

From these two parameters, it can be concluded that the reduction in water and electrolyte loss was clearly superior with ORS+Attapulgite than with ORS alone; there is thus a reduction in the risk of dehydration. This combination also provides a certain degree of reassurance for the mothers.

(3) Evolution of body weight curves over 48 hours

These results are given in the table below:

| | 0 | +50-100 g /day | +100-150 g /day | +150-250 g /day | +250-350 g /day | LOSS |
| --- | --- | --- | --- | --- | --- | --- |
| ORS | 0 | 35 | 14 | 0 | 0 | 1 |
| ORS + ATTA | 2 | 3 | 18 | 25 | 2 | 0 |

There was regular weight gain in 49 of the children in the ORS group and 48 in the ORS+ATTA group. In the ORS group, only a single child with malnutrition showed an aggravation of diarrhea over the first 48 hours, with a loss of 50 g/day.

For the other children in the ORS group, there was constant and gradual weight gain, with a mean gain of 100-200 g/day and a rapid improvement in general status.

In the group treated with ORS+Attapulgite, diarrhea worsened in 2 malnourished children, but without further weight loss. In all others, weight gain was a mean 150-250/day, and in a few cases, 300 g or more.

In view of these results it can be stated that weight gain in both groups was satisfactory.

(4) Duration of treatment

This was calculated as the time between the beginning of the treatment and normalization of digestive symptomatology. The results are given in the table below.

| Number of days' treatment | ORS | | ORS + ATTA | |
|---|---|---|---|---|
| 3 days | 3 | 6% | 8 | 16% |
| 4 days | 6 | 12% | 38 | 76% |
| 5 days | 13 | 26% | 4 | 8% |
| 6 days | 28 | 56% | 0 | — |

In the ORS group, mean duration of treatment ranged between 5 and 6 days, while in the ORS+ATTA group, it ranged between 3 and 4 days.

There was thus a major difference between the required duration of treatment with ORS and with the combination. This yielded both an improvement in treatment, and the liberation of a number of hospital beds, of great importance in many situations.

The experimentation was repeated with the composition 5 on two groups of 10 patients with comparable results reported in the following tables:

| Characteristics of Stools after 48 hours treatment | | | | |
|---|---|---|---|---|
| | ORS (n = 50) | | ORS + activated Smectite (n = 50) | |
| | No. | % | No. | % |
| Liquid stools | 5 | 50 | 2 | 20 |
| Semi-liquid stools | 2 | 20 | 3 | 30 |
| Soft stools | 2 | 20 | 4 | 40 |
| Normal stools | 1 | 10 | 1 | 10 |

| Number of stools per day after 48 hours treatment | | |
|---|---|---|
| | MEAN NUMBER OF STOOLS/DAY | |
| Product | Upon admission | After 48 hours treatment |
| ORS | 6 | 4 |
| ORS + activated Smectite | 6 | 3 |

| Evolution of body weight curves over 48 hours | | | | | |
|---|---|---|---|---|---|
| | 0 | +50–100 g /day | +100–150 g /day | +150–250 g /day | +250–350 g /day |
| ORS | 1 | 7 | 2 | 0 | 0 |
| ORS + activated Smectite | 0 | 1 | 3 | 5 | 1 |

(5) Relapses

Any recurrence of diarrhea 3 days after resolution was labeled a relapse. In the experiment described herein, there were 7 relapses in the ORS group and only 2 In the ORS+ATTA group and none in the ORS+activated smectite group.

(6) Side effects

There were a few cases of constipation in the ORS+Attapulgite group and none in the ORS+activated smectite group, in particular at the beginning of the study, in children weighing approximately 5 kg, for whom the dose of 2 envelopes/day was probably somewhat excessive.

(7) Cost of treatment

This was an important consideration, and given the current situation it is impossible to ignore this question in African public health programs, where it is possible to choose a given treatment modality only if it is sufficiently inexpensive. Treatment with ORS and attapulgite, although more expensive per treatment than the use of ORS alone, is nonetheless acceptably inexpensive, particularly as compared to treatments such as intravenous drug and electrolyte administration.

Safety of ORS+ATTA treatment also was good; the few cases of constipation seen in very young children required a decrease in dosage, and did not constitute major therapeutic obstacles.

We claim:

1. A method of treating diarrhea in a human patient comprising administering to said patient diarrhea symptom-reducing amounts of first and second compositions, said first and second compositions being admixed together, or administered separately within thirty minutes of each other, said first composition comprising a powdered absorptive material capable of absorbing pathogenic intestinal bacteria, said powdered absorptive material being a thermally activated, finely powdered, hydrous magnesium aluminum silicate clay, and said second composition comprising an oral rehydration salt comprising a sodium salt, a potassium salt, and a sugar, at least said second composition being administered to said patient admixed with water.

2. The composition of claim 1 wherein said composition further comprises a dessicating agent.

3. The composition of claim 1, further comprising a suspending agent capable of facilitating the suspension of said absorptive material in water.

4. The composition of claim 3, wherein said suspending agent is a hydrocolloid, a polyol, or a surfactant.

5. The composition of claim 4, wherein said suspending agent comprises one of the hydrocolloids sodium carboxy methyl cellulose, xanthan gum, hydroxy propyl methyl cellulose, polyethylene glycol, a dextrin, gum karaya, gum tragacanth, gum acacia, gum guar, or a polysaccharide.

6. The composition of claim 4, wherein said suspending agent comprises one of the polyols glycerin, propylene glycol, or sorbitol.

7. The composition of claim 4, wherein said suspending agent comprises one of the surfactants dioctyl sulfosuccinate, polysorbate-40, or sorbitan monooleate.

8. The composition of claim 1, wherein said sodium and potassium salts are pre-treated to inhibit moisture absorption.

9. The composition of claim 8, in a package consisting essentially of waxed paper.

10. The composition of claim 1, in a water-resistant package.

11. The method of claim 1, wherein the human patients treated are children and wherein
   (a) said first composition is in liquid solution and is present in the amount of 2.5 to 15 g per liter of liquid material;
   (b) said second composition is in liquid solution and comprises, per liter of solution, 10–30 g glucose, 60–120 mEq of sodium, 10–30 mEq of potassium and 10–50 mEq of bicarbonate;
   and wherein the two compositions are admixed and are administered at the rate of one-quarter to one-half liter for children younger than 6 months and one-half to one liter for children between 6 and 24 months.

12. The method of claim 1 wherein the first composition is derived from Smectite and the second composition comprises glucose, sodium bicarbonate, potassium chloride and sodium chloride.

* * * * *